United States Patent
Yajima et al.

(10) Patent No.: US 9,315,839 B2
(45) Date of Patent: Apr. 19, 2016

(54) PROCESSES FOR PRODUCING COENZYME $Q_{10}$

(75) Inventors: Kazuyoshi Yajima, Hyogo (JP); Takahisa Kato, Hyogo (JP); Akihisa Kanda, Osaka (JP); Shiro Kitamura, Hyogo (JP); Yasuyoshi Ueda, Hyogo (JP)

(73) Assignee: KANEKA CORPORATION, Osaka (JP)

( * ) Notice: Subject to any disclaimer, the term of this patent is extended or adjusted under 35 U.S.C. 154(b) by 420 days.

(21) Appl. No.: 13/020,500

(22) Filed: Feb. 3, 2011

(65) Prior Publication Data

US 2011/0136191 A1 Jun. 9, 2011

Related U.S. Application Data

(62) Division of application No. 11/981,181, filed on Oct. 31, 2007, now Pat. No. 7,910,340, which is a division of application No. 10/500,249, filed as application No. PCT/JP02/13766 on Dec. 27, 2002, now abandoned.

(30) Foreign Application Priority Data

Dec. 27, 2001 (JP) .................................. 2001-398545

(51) Int. Cl.
    *C12P 7/66* (2006.01)
    *C12P 7/22* (2006.01)
(52) U.S. Cl.
    CPC ..... *C12P 7/66* (2013.01); *C12P 7/22* (2013.01)
(58) Field of Classification Search
    None
    See application file for complete search history.

(56) References Cited

U.S. PATENT DOCUMENTS

| | | | |
|---|---|---|---|
| 3,066,080 A | 11/1962 | Folkers | |
| 3,769,170 A | 10/1973 | Kondo et al. | |
| 4,220,719 A | 9/1980 | Aida et al. | |
| 6,156,802 A | 12/2000 | Mae et al. | |

FOREIGN PATENT DOCUMENTS

| | | | |
|---|---|---|---|
| DE | 236552 | A1 | 11/1986 |
| EP | 0051921 | A1 | 5/1982 |
| EP | 0073134 | A2 | 3/1983 |
| EP | 0956854 | A1 | 11/1999 |
| EP | 1123979 | A1 | 8/2001 |
| EP | 1336657 | A1 | 8/2003 |
| EP | 1354957 | A1 | 10/2003 |
| EP | 1386905 | A1 | 2/2004 |
| EP | 1391515 | A1 | 2/2004 |
| EP | 1408024 | A1 | 4/2004 |
| EP | 1415969 | A1 | 5/2004 |
| EP | 1415970 | A1 | 5/2004 |
| EP | 1415971 | A1 | 5/2004 |
| EP | 1415972 | A1 | 5/2004 |
| EP | 1415973 | A1 | 5/2004 |
| EP | 1440962 | A1 | 7/2004 |
| EP | 1452174 | A1 | 9/2004 |
| GB | 930752 | A | 7/1963 |
| JP | 48-8836 | B | 3/1973 |
| JP | 48-25517 | A | 7/1973 |
| JP | 54-52790 | A | 4/1979 |
| JP | 54-110388 | A | 8/1979 |
| JP | 54-119090 | A | 9/1979 |
| JP | 55-000027 | A | 1/1980 |
| JP | 55-000028 | A | 1/1980 |
| JP | 55-21756 | A | 2/1980 |
| JP | 55-048397 | A | 4/1980 |
| JP | 55-68295 | A | 5/1980 |
| JP | 55-148084 | A | 11/1980 |
| JP | 56-55196 | A | 5/1981 |
| JP | 56-154994 | A | 11/1981 |
| JP | 56-154996 | A | 11/1981 |
| JP | 57-33599 | A | 2/1982 |
| JP | 57-70834 | A | 5/1982 |
| JP | 60-075294 | A | 4/1985 |
| JP | 60-75294 | A | 4/1985 |
| JP | 61-271994 | A | 12/1986 |
| JP | 63-36789 | A | 2/1988 |
| JP | 63-102691 | A | 5/1988 |
| JP | 63-317092 | A | 12/1988 |
| JP | 10-57072 | A | 3/1998 |
| JP | 10-109933 | A | 4/1998 |
| JP | 10-330251 | A | 12/1998 |
| JP | 11-056372 | A | 3/1999 |

(Continued)

OTHER PUBLICATIONS

Takada, Masahiro et al "Studies on Reduced and Oxidized Coenzyme Q (Ubiquinones): The Determination of Oxidation-Reduction Levels of Coenzyme Q in Mitochondria, Microsomes and Plasma by High-Performance Liquid Chromatography," Biochimica et Biophysica Acta, 1982, vol. 679, pp. 308-314.

(Continued)

*Primary Examiner* — Vera Afremova
(74) *Attorney, Agent, or Firm* — Westerman, Hattori, Daniels & Adrian, LLP

(57) ABSTRACT

The present invention relates to a process for producing reduced coenzyme $Q_{10}$ which comprises obtaining microbial cells containing reduced coenzyme $Q_{10}$ at a ratio of not less than 70 mole % among the entire coenzymes $Q_{10}$, optionally disrupting the cells and recovering thus produced reduced coenzyme $Q_{10}$. The present invention also relates to a process for producing oxidized coenzyme $Q_{10}$ which comprises either recovering oxidized coenzyme $Q_{10}$ after oxidizing the above-mentioned microbial cells or disrupted product thereof, or recovering reduced coenzyme $Q_{10}$ from the above-mentioned microbial cells or disrupted product thereof to oxidize thus-obtained reduced coenzyme $Q_{10}$ thereafter. According to the processes of the present invention, reduced coenzyme $Q_{10}$ and oxidized coenzyme $Q_{10}$ can be produced simply on the industrial scale.

24 Claims, 1 Drawing Sheet

(56) References Cited

FOREIGN PATENT DOCUMENTS

| JP | 2001-61478 B1 | 3/2001 |
|---|---|---|
| JP | 2004-266130 A | 9/2004 |
| JP | 2012-157360 A | 8/2012 |
| WO | 96/17626 | 6/1996 |
| WO | 01/27286 A1 | 4/2001 |

OTHER PUBLICATIONS

Yoshida, Hajime et al "Production of ubiquinone-10 using bacteria," J. Gen. Microbiol. 1998, vol. 44, pp. 19-26.

Disch, Andrea et al., "On the Absence of the Glyceraldehyde 3-Phosphate/Pyruvate Pathway for Isoprenoid Biosynthesis in Fungi and Yeasts," FEMS Microbiology Letters, vol. 168, No. 2, 1998, pp. 201-208.

Kockova-Kratochvilova, A. et al., "Die Beziehungen innerhalb der Gattung Cryptococcus (Sanfelice) Vuillemin", Zbl. Bakt. Abt. 11, Bd., vol. 131, No. 7, 1976, pp. 610-631.

Natori, Y. et al., "Production of Coenzyme Qlo by Pseudomonas N842", Agric. Biol. Chem., vol. 42, No. 9, 1978, pp. 1799-1800.

Natori, Y. et al., "Enhancement of Coenzyme Q10 Accumulation by Mutation and Effects of Medium Components on the Formation of Coenzyme Q Homologs by Pseudomonas N842 and Mutants", Agric. Biol. Chem., vol. 45, No. 10, 1981, pp. 2175-2182.

Ohta, H. et al., "*Agromonas oligotrophica* gen. nov., sp. nov., a Nitrogen-Fixing Oligotrophic Bacterium", Antonie van Leeuwenhoek, vol. 49, Nos. 4-5, 1983, pp. 429-446.

Sakato, K. et al., "Agitation-Aeration Studies on Coenzyme Q10 Production Using Rhodopseudomonas spheroides," Biotechnology and Applied Biochemistry, vol. 16, No. 1, 1992, pp. 19-28.

Urakami T., et al., "Production of Isoprenoid Compounds in the Facultative Methylotroph Protomonas extroquens", J. Ferment. Technol., vol. 66, No. 3, 1988, pp. 323-332.

Urakami, T. et al., "Production of Ubiquinone and Bacteriochlorophyll & by Rhodobacter sphaeroides and Rhodobacter sulfidophilus", Journal of Fermentation and Bioengineering, vol. 76, No. 3, 1993, pp. 191-194.

Urakami, T., et al., "Transfer of Pseudomonas aminovorans (den Dooren de Jong 1926) to Aminobacter gen. nov. as *Aminobacter aminovorans* comb. nov. and Description of *Aminobacter aganoensis* sp. nov. and *Aminobacter niigataensis* sp. nov.", International Journal of Systematic Bacteriology, vol. 42, No. 1, Jan. 1992, pp. 84-92.

Venturoli et al., Biochimica et Biophysica Acta, 935 (1 988) pp. 258-272.

Wakabayashi et al., Biol. Pharm. Bull., 1994, 17(8):997-1002.

Wakao, N. et al., "*Acidiphilium multivorm* sp. nov., an Acidophilic Chemoorganotrophic Bacterium from Pyritic Acid Mine Drainage", Journal of General and Applied Microbiology, vol. 40, No. 2, 1994, pp. 143-1 59.

Yabuuchi, E., et al., "Proposals of *Sphingomonas paucimobilis* gen. nov. and comb. nov., *Sphingomonas parapaucimobilis* sp. nov., *Sphingomonas yanoikuyae* sp. nov., *Sphingomonas adhaesiva* sp. nov., Sphingomonas capsulata comb. nov., and Two Genospecies of the Genus *Sphingomonas*," Microbiology and Immunology, vol. 34, No. 2, 1 990, pp. 99-1 1 9.

Yamada, Y., et al., "The Coenzyme Q System in Strains of *Trichosporon* Species and Related Organisms", Journal of General and Applied Microbiology, vol. 28, No. 4, 1982, pp. 355-358.

Yoshida, H. et al. "Production of Ubiquinone-10 Using Bacteria J", Journal of General and Applied Microbiology, vol. 44, No. 1, 1998, pp. 19-26.

International Search Report from corresponding International Application No. PCT/JPO2/113766, dated Apr. 15, 2003.

Takashi Sugita et al., "Reclassification of Trichosporon Cutaneum by DNA Relatedness by the Spectrophotometric Method and the Chemiluminometric Method", Journal of General and Applied Microbiology, 1994, vol. 40, pp. 397-408, cited in Japanese Reconsideration Report dated Oct. 1, 2014, issued in corresponding JP application No. 2012-094126 (12 pages).

Yuzo Yamada et al., "Coenzyme Q System in the Classification of the Ascosporogenous Yeast Genus *Schizosaccharomyces* and Yeast-Like Genus *Endomyces*", Journal of General and Applied Microbioiogy, 1973; vol. 19, pp. 353-358, cited in Japanese Reconsideration Report dated Oct. 1, 2014; issued in corresponding JP application No. 2012-094126 (6 pages).

Reexam Order dated Dec. 16, 2015, issued in U.S. Pat. No. 7,910,340 (Control No. 90/013,636). (9 pages).

Urakami, Teizi et al. Occurrence of Isoprenoid Compounds in Gram-Negative Methanol-, Methane-, and Methylamine-Utilizing Bacteria, 32 J Gen. & Applied Microbiology 317, 317-341 (1986).

National Fire Protection Association (NFPA) 36—" Standard for Solvent Extraction Plants" (1997 Edition).

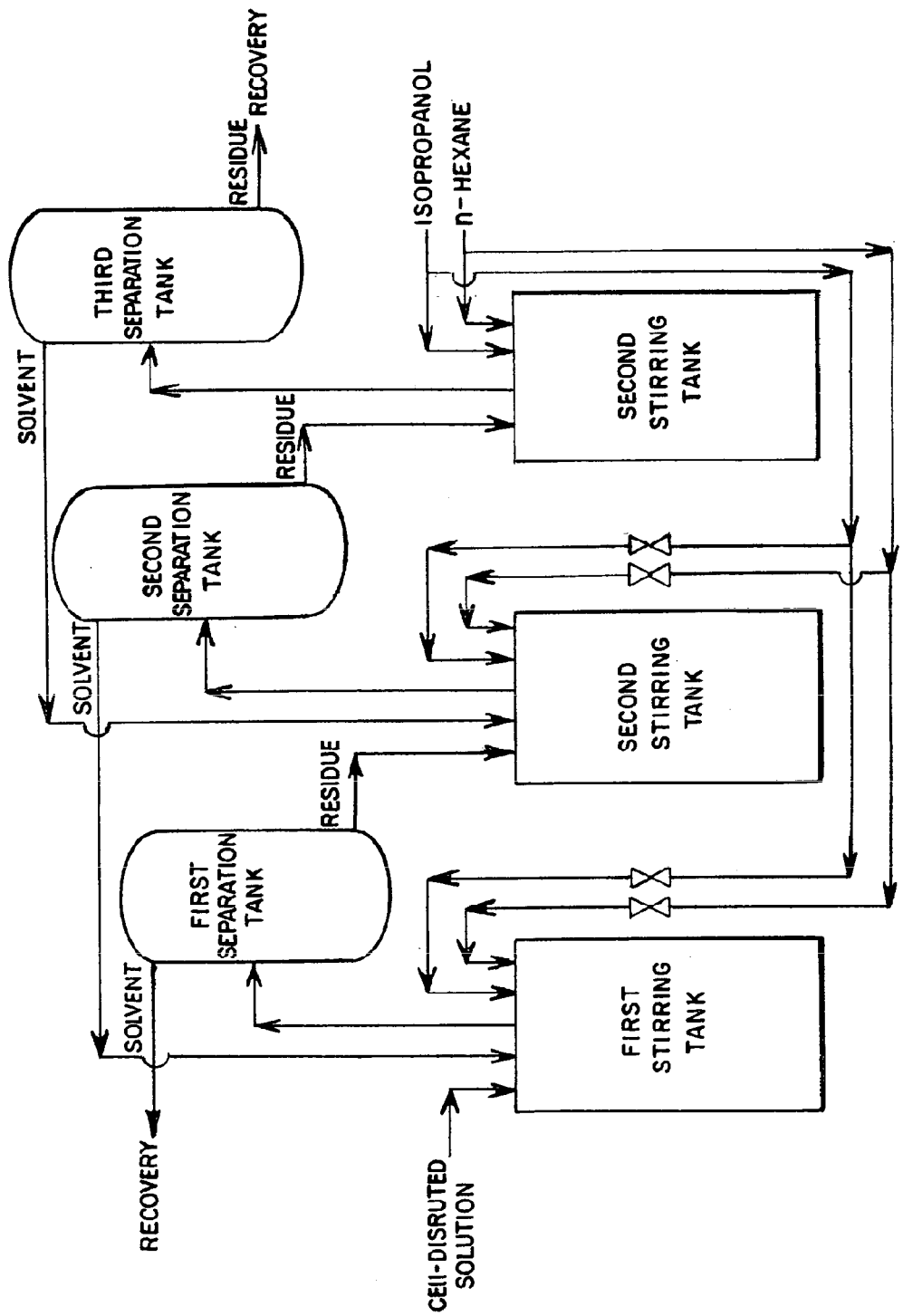

PROCESSES FOR PRODUCING COENZYME $Q_{10}$

RELATED APPLICATIONS

This application is a divisional of U.S. application Ser. No. 11/981,181, filed Oct. 31, 2007, which is in turn a divisional of Ser. No. 10/500,249, filed Nov. 3, 2004, which is based on and claims priority of International Application No. PCT/JP2002/13766 filed Dec. 27, 2002, and on Japanese Patent Application No. JP2001-398545, filed Dec. 27, 2001, each of which is incorporated herein in its entirety by reference.

TECHNICAL FIELD

The present invention relates to
a process for producing the reduced coenzyme $Q_{10}$ represented by the following formula (I):

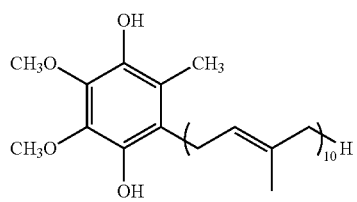

and a process for producing the oxidized coenzyme $Q_{10}$ represented by the following formula (II):

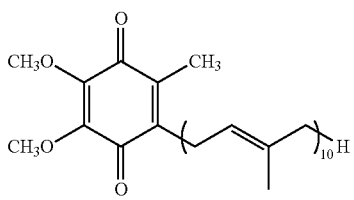

More particularly, the present invention relates to
a process for producing reduced coenzyme $Q_{10}$
which comprises culturing reduced coenzyme $Q_{10}$-producing microorganisms to obtain microbial cells containing reduced coenzyme $Q_{10}$ at a ratio of not less than 70 mole % among the entire coenzymes $Q_{10}$,
optionally disrupting the microbial cells and recovering thus-produced reduced coenzyme $Q_{10}$.

The present invention also relates to a process for producing oxidized coenzyme $Q_{10}$ which comprises either recovering oxidized coenzyme $Q_{10}$ after oxidizing the above-mentioned microbial cells or disrupted product thereof, or recovering reduced coenzyme $Q_{10}$ from the above-mentioned microbial cells or disrupted product thereof to oxidize thus-obtained reduced coenzyme $Q_{10}$ thereafter.

BACKGROUND ART

The reduced coenzyme $Q_{10}$ (I) and the oxidized coenzyme $Q_{10}$ (II) are mitochondrial electron transport system-constituting factors in cells of a living body of human and deal with ATP production by working as electron carriers in oxidative phosphorization reactions.

Conventionally, oxidized coenzyme $Q_{10}$ has been widely used for supplementary nutrient foods and cosmetic products in addition to pharmaceutical products as a pharmaceutically and physiologically effective substance for a variety of diseases.

On the other hand, reduced coenzyme $Q_{10}$ has not so much drawn attention so far; however, in these years, there has been reported that reduced coenzyme $Q_{10}$ is more effective in various applications than oxidized coenzyme $Q_{10}$.

For example, Japanese Kokai Publication Hei-10-330251 discloses an antihypercholesterolemia agent having excellent cholesterol reducing function, an antihyperlipemia agent, and an agent for curing and preventing arteriosclerosis which contain reduced coenzyme $Q_{10}$ as an active ingredient. In addition, Japanese Kokai Publication Hei-10-109933 discloses a pharmaceutical composition excellent in oral absorbability comprising coenzyme $Q_{10}$ including reduced coenzyme $Q_{10}$ as an active ingredient.

Furthermore, reduced coenzyme $Q_{10}$ is effective as an antioxidant and a radical scavenger. R. Stocker, et al. have reported that reduced coenzyme $Q_{10}$ prevented peroxidation of human LDL more efficiently than α-tocopherol, lycopene and β-carotene (Proceedings of the National Academy of Science of the United States of America, vol. 88, pp. 1646-1650, 1991).

It has been known that oxidized coenzyme $Q_{10}$ and reduced coenzyme $Q_{10}$ are in a certain type of equilibrium in a living body and that oxidized coenzyme $Q_{10}$/reduced coenzyme $Q_{10}$ absorbed in the living body are mutually reduced/oxidized.

Reduced coenzyme $Q_{10}$ is supposedly produced by a chemical synthesis method, similarly to the process for producing oxidized coenzyme $Q_{10}$. But the synthesis process is supposed to be complicated, risky and costly. Moreover, in the case of chemical synthesis methods, it will be necessary to minimize the subgeneration and contamination of a (Z)-isomer, which is suspiciously unsafe (Biomedical and Clinical Aspects of Coenzyme Q, vol. 3, pp. 19-30, 1981). Europe Pharmacopoeia regulates that a content of (Z)-isomer in oxidized coenzyme $Q_{10}$ must be not more than 0.1%.

As another process for producing reduced coenzyme $Q_{10}$, it can be supposed a method of utilizing microbial cells, that is, a method for separating and recovering reduced coenzyme $Q_{10}$ from reduced coenzyme $Q_{10}$-producing microorganisms. However, the reduced coenzyme $Q_{10}$ produced by the microbial cells of the above-mentioned microorganisms contains a large amount of oxidized coenzyme $Q_{10}$, and the separation and recovery of reduced coenzyme $Q_{10}$ by a conventional method results in high cost.

The following are documents describing the presence of reduced coenzyme $Q_{10}$ in microbial cells and there have been known the following examples of bacteria.

(1) An example describing that at lowest 5 to 10% by weight and at highest 30 to 60% by weight of reduced coenzyme $Q_{10}$ are present among the entire coenzymes $Q_{10}$ in culture cells of photosynthesis bacteria (Japanese Kokai Publication Sho-57-70834).

(2) An example describing that the genus *Pseudomonas* is subjected to thermal extraction by an organic solvent in the presence of sodium hydroxide and pyrogallol, and the resultant is treated with 5% sodium hydrosulfite solution, and further dehydrated and concentrated to collect an acetone-soluble portion, and an oil containing reduced coenzyme $Q_{10}$ is obtained (Japanese Kokai Publication Sho-60-75294).

Both of the above (1) and (2) aim to convert a mixture of the obtained reduced coenzyme $Q_{10}$ and oxidized coenzyme $Q_{10}$ or the obtained reduced coenzyme $Q_{10}$ into oxidized coenzyme $Q_{10}$ by further oxidation. Thus, reduced coenzyme $Q_{10}$ is only described as an intermediate substance in producing oxidized coenzyme $Q_{10}$.

In the above (1), photosynthesis bacteria are used, the culture of which is complicated. Furthermore, in the microbial cells of the above-mentioned microorganisms, when the production of reduced coenzyme $Q_{10}$ is aimed at, it cannot be said that the ratio of reduced coenzyme $Q_{10}$ among the entire coenzymes $Q_{10}$ is sufficient.

The above (2) comprises a process of converting oxidized coenzyme $Q_{10}$ contained in a hexane phase into reduced coenzyme $Q_{10}$ by sodium hydrosulfite, a reducing agent (see Example 3 in Japanese Kokai Publication Sho-60-75294). Thus, the ratio of reduced coenzyme $Q_{10}$ among the entire coenzymes $Q_{10}$ in the microbial cells is not clear.

Furthermore, in both of the above (1) and (2), the production amount of coenzymes Q in culture are not described.

As described above, microbial cells containing reduced coenzyme $Q_{10}$ at high ratio have not been reported yet. Still less, it has not been known a fermentation production of reduced coenzyme $Q_{10}$ on the industrial scale, that is, a method comprising culturing microorganisms to obtain microbial cells containing reduced coenzyme $Q_{10}$ at high ratio among the entire coenzymes $Q_{10}$, and recovering reduced coenzyme $Q_{10}$ to obtain high-purity reduced coenzyme $Q_{10}$.

Under such circumstances, if a method for obtaining a large quantity of coenzyme $Q_{10}$ containing reduced coenzyme $Q_{10}$ at high ratio by culturing microorganisms is found, it can be a highly useful method for producing reduced coenzyme $Q_{10}$.

SUMMARY OF THE INVENTION

It is an object of the present invention to provide a process for producing reduced coenzyme $Q_{10}$ safely and efficiently on the industrial scale by culturing reduced coenzyme $Q_{10}$-producing microorganisms for obtaining microbial cells containing reduced coenzyme $Q_{10}$ at high ratio and suitably recovering reduced coenzyme $Q_{10}$ from the microbial cells.

It is another object of the present invention to provide a process for producing oxidized coenzyme $Q_{10}$ in simple processes by culturing reduced coenzyme $Q_{10}$-producing microorganisms for obtaining microbial cells containing reduced coenzyme $Q_{10}$ at high ratio, and oxidizing the reduced coenzyme $Q_{10}$ obtained from the microbial cells as an intermediate substance in producing oxidized coenzyme $Q_{10}$.

That is, the present invention relates to a process for producing the reduced coenzyme $Q_{10}$ represented by the following formula (I):

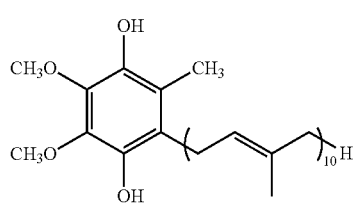

which comprises culturing reduced coenzyme $Q_{10}$-producing microorganisms in a culture medium containing a carbon source, a nitrogen source, a phosphorus source and a micronutrient to obtain microbial cells containing reduced coenzyme $Q_{10}$ at a ratio of not less than 70 mole % among the entire coenzymes $Q_{10}$, optionally disrupting the microbial cells and extracting thus-produced reduced coenzyme $Q_{10}$ by an organic solvent.

Furthermore, the present invention also relates to a process for producing the oxidized coenzyme $Q_{10}$ represented by the following formula (II):

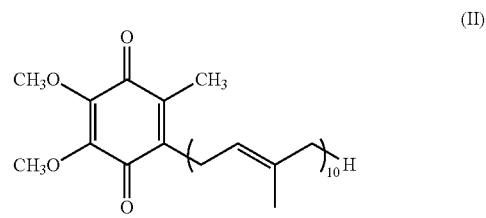

which comprises culturing reduced coenzyme $Q_{10}$-producing microorganisms in a culture medium containing a carbon source, a nitrogen source, a phosphorus source and a micronutrient to obtain microbial cells containing reduced coenzyme $Q_{10}$ at a ratio of not less than 70 mole % among the entire coenzymes $Q_{10}$, optionally disrupting the microbial cells; and either oxidizing thus-produced reduced coenzyme $Q_{10}$ to oxidized coenzyme $Q_{10}$ and then extracting the resultant by an organic solvent, or extracting thus-produced reduced coenzyme $Q_{10}$ by an organic solvent, purifying optionally and oxidizing the resultant to oxidized coenzyme $Q_{10}$.

According to the processes of the present invention, reduced coenzyme $Q_{10}$ can be produced cheaply on the industrial scale by considerably simple steps comprising culturing microorganisms and recovering reduced coenzyme $Q_{10}$. In addition, oxidized coenzyme $Q_{10}$ can also be produced by simple processes. Moreover, these coenzymes $Q_{10}$ produced by microorganisms basically do not contain (Z)-isomers thereof, and (all-E) isomers thereof can be obtained, which are same as those contained in meat, fish, etc.

DETAILED DESCRIPTION OF THE INVENTION

In the present invention, at first, reduced coenzyme $Q_{10}$-producing microorganisms are cultured to obtain microbial cells containing reduced coenzyme $Q_{10}$ at a ratio of not less than 70 mole %, preferably not less than 75 mole %, among the entire. coenzymes $Q_{10}$ (fermentation).

The microbial cells containing reduced coenzyme $Q_{10}$ at such high ratio among the entire coenzymes $Q_{10}$ can be basically obtained by culturing microorganisms capable of producing reduced coenzyme $Q_{10}$ at a ratio of not less than 70 mole %, preferably not less than 75 mole %, among the entire coenzymes $Q_{10}$.

How much ratio the microorganisms can produce reduced coenzyme $Q_{10}$ among the entire coenzymes $Q_{10}$ can be evaluated, for example, by a method comprising culturing the microorganisms with shaking (amplitude: 2 cm, 310 reciprocation/min) at 25° C. for 72 hours in 10 mL of a culture medium [(glucose: 20 g, peptone: 5 g, yeast extract: 3 g, malt extract: 3 g)/L, pH: 6.0] using a test tube (inner diameter: 21 mm, entire length: 200 mm).

Although the preferable culture conditions for the fermentation production on the industrial scale will be described later, the above-mentioned culture condition is one method for standardizing the ratio of reduced coenzyme $Q_{10}$ produced, which microorganisms have as its ability, so as to reflect the ratio within the range without having significant inaccuracies.

Under the above-mentioned culture condition, it is preferable to use microbial cells wherein a content of reduced coenzyme $Q_{10}$ is at a ratio of not less than 70 mole %, preferably not less than 75 mole %, among the entire coenzymes $Q_{10}$, for the present invention. It is still more preferable to use microorganisms having a productivity of reduced coenzyme $Q_{10}$ per unit culture medium of generally not less than 1 μg/mL, preferably not less than 2 μg/mL under the above-mentioned culture condition.

The above-mentioned content of reduced coenzyme $Q_{10}$ and ratio of reduced coenzyme $Q_{10}$ among the entire coenzymes $Q_{10}$ can be confirmed by physically disrupting the microbial cells, extracting coenzyme $Q_{10}$ from thus-obtained cells by an organic solvent and performing HPLC analysis. Specifically, the measurement can be carried out according to the following procedures:

(1) The broth of microorganism is optionally concentrated, 10 parts by volume of the broth are displaced to a screw cap test tube (inner diameter: 16.5 mm, entire length: 130 mm), and 10 parts by volume of glass beads are added (425 to 600 μm, manufactured by SIGMA Co.);
(2) 3 parts by volume of isopropanol and 18.5 parts by volume of n-hexane relative to 10 parts by volume of the broth are added under a nitrogen atmosphere;
(3) microbial cell disruption and extraction are carried out by vigorously shaking of the mixture for 3 minutes under a nitrogen atmosphere; and
(4) the obtained hydrophobic organic solvent phase (n-hexane phase) is evaporated (bath temperature: 40° C.) under reduced pressure to analyze the resultant by HPLC.

Column: YMC-Pack 4.6×250 mm (manufactured by YMC. Co., Ltd.)
Mobile phase: methanol/n-hexane=85/15
Flow rate: 1 mL/min,
Detection: UV 275 nm
Retention time: reduced coenzyme $Q_{10}$ 13.5 min
oxidized coenzyme $Q_{10}$ 22.0 min The above-mentioned measurement method is provided for the obtained result to reflect the reduced coenzyme $Q_{10}$ content and the ratio of reduced coenzyme $Q_{10}$ among the entire coenzymes $Q_{10}$ as accurate as possible, and to standardize the content and the ratio of reduced coenzyme $Q_{10}$, which can be guaranteed at the minimum. This method has been demonstrated, by several experimentations performed by the present inventors, easy and suitable to be carried out.

As the above-mentioned reduced coenzyme $Q_{10}$-producing microorganisms to be used in the present invention, bacteria, yeast and fungi may be used without any specific limitation. As specific examples of the above-mentioned microorganisms, there may be mentioned, for example, microorganisms of the genus *Agrobacterium*, the genus *Aspergillus*, the genus *Acetobacter*, the genus *Aminobacter*, the genus *Agromonas*, the genus *Acidiphilium*, the genus *Bulleromyces*, the genus *Bullera*, the genus *Brevundimonas*, the genus *Cryptococcus*, the genus *Chionosphaera*, the genus *Candida*, the genus *Cerinosterus*, the genus *Exisophiala*, the genus *Exobasidium*, the genus *Fellomyces*, the genus *Filobasidiella*, the genus *Fliobasidium*, the genus *Geotrichum*, the genus *Graphiola*, the genus *Gluconobacter*, the genus *Kockovaella*, the genus *Kurtzmanomyces*, the genus *Lalaria*, the genus *Leucosporidium*, the genus *Legionella*, the genus *Methylobacterium*, the genus *Mycoplana*, the genus *Oosporidium*, the genus *Pseudomonas*, the genus *Psedozyma*, the genus *Paracoccus*, the genus *Petromyces*, the genus *Rhodotorula*, the genus *Rhodosporidium*, the genus *Rhizomonas*, the genus *Rhodobium*, the genus *Rhodoplanes*, the genus *Rhodopseudomonas*, the genus *Rhodobacter*, the genus *Sporobolomyces*, the genus *Sporidiobolus*, the genus *Saitoella*, the genus *Schizosaccharomyces*, the genus *Sphingomonas*, the genus *Sporotrichum*, the genus *Sympodiomycopsis*, the genus *Sterigmatosporidium*, the genus *Tapharina*, the genus *Tremella*, the genus *Trichosporon*, the genus *Tilletiaria*, the genus *Tilletia*, the genus *Tolyposporium*, the genus *Tilletiopsis*, the genus *Ustilago*, the genus *Udeniomyces*, the genus *Xanthophilomyces*, the genus *Xanthobacter*, the genus *Paecilomyces*, the genus *Acremonium*, the genus *Hyhomonus*, and the genus *Rhizobium*.

In terms of the culture easiness and productivity, bacteria (preferably nonphotosynthetic bacteria) and yeast are preferred. As the bacteria, there may be mentioned, for example, the genus *Agrobacterium*, the genus *Gluconobacter* and the like. As the yeast, there may be mentioned, for example, the genus *Schizosaccharomyces*, the genus *Saitoella* and the like.

As preferable species, there may be mentioned, for example, *Agrobacterium tumefacience* IFO13263, *Agrobacterium radiobacter* ATCC4718, *Aspergillus clavatus* JCM1718, *Acetobacter xylinum* IFO15237, *Aminobacter aganouensis* JCM7854, *Agromonas oligotrophica* JCM1494, *Acidiphilium multivorum* JCM8867, *Bulleromyces albus* IFO1192, *Bullera armeniaca* IFO10112, *Brevundimonas diminuta* JCM2788, *Cryptococcus laurentii* IFO0609, *Chionosphaera apobasidialis* CBS7430, *Candida curvata* ATCC10567, *Cerinosterus luteoalbus* JCM2923, *Exisophiala alcalophila* JCM12519, *Exobasidium gracile* IFO7788, *Fellomyces fuzhouensis* IFO10374, *Filobasidiella neoformans* CBS132, *Filobasidium capsuloigenum* CBS1906, *Geotrichum capitatum* JCM6258, *Graphiola cylindrica* IFO6426, *Gluconobacter suboxydans* IFO3257, *Kockovaella imperatae* JCM7826, *Kurtzmanomyces nectairei* IFO10118, *Lalaria cerasi* CBS275.28, *Leucosporidium scottii* IFO1212, *Legionella anisa* JCM7573, *Methylobacterium extorguens* JCM2802, *Mycoplana ramosa* JCM7822, *Oosporidium margaritiferum* CBS2531, *Pseudomonas denitrificans* IAM 12023, *Pseudomonas shuylkilliensis* IAM 1092, *Psedozyma aphidis* CBS517.23, *Paracoccus denitrificans* JCM6892, *Petromyces alliaceus* IFO7538, *Rhodotorula glutinis* IFO1125, *Rhodotorula minuta* IFO0387, *Rhodosporidium diobovatum* ATCC1830, *Rhizomonas suberifaciens* IFO15212, *Rhodobium orients* JCM9337, *Rhodoplanes elegans* JCM9224, *Rhodopseudomonas palustris* JCM2524, *Rhodobacter capsulatus* SB1003, *Sporobolomyces holsaticus* IFO1034, *Sporobolomyces pararoseus* IFO0471, *Sporidiobolus johnsonii* IFO1840, *Saitoella complicata* IFO10748, *Schizosaccharomyces pombe* IFO0347, *Sphingomonas parapaucimobilis* IFO15100, *Sporotrichum cellulophilium* ATCC20493, *Sympodiomycopsis paphiopedili* JCM8318, *Sterigmatosporidium polymorphum* IFO10121, *Sphingomonas adhesiva* JCM7370, *Tapharina caerulescens* CBS351.35, *Tremella mesenterica* ATCC24438, *Trichosporon cutaneum* IFO1198, *Tilletiaria anomala* CBS436.72, *Tilletia caries* JCM1761, *Tolyposporium bullatum* JCM2006, *Tilletiopsis washintonesis* CBS544, *Ustilago esculenta* IFO9887, *Udeniomyces megalosporus* JCM5269, *Xanthophilomyces dendrorhous* IFO10129, *Xanthobacter flavus* JCM1204, *Paecilomyces lilacinus* ATCC10114, *Acremonium chrysogenum* ATCC11550, *Hyphomonas hirschiana* ATCC33886, *Rhizobium meliloti* ATCC9930, and the like.

As the reduced coenzyme $Q_{10}$-producing microorganisms, not only the wild species of the above-mentioned microorganisms but also microorganisms in which the transcription and translation activities of the genes relevant to the biosynthesis of reduced coenzyme $Q_{10}$ in the above-mentioned microorganisms, or the enzyme activity of the expressed protein are modified or improved can be used preferably, for example.

As the means for modifying or improving the transcription and translation activities of the genes or the enzyme activity of the expressed protein, there may be mentioned gene recombination (including gene improvement, amplification and destruction by itself, external gene introduction, and gene improvement and proliferation of thus-introduced external genes) and mutagenesis by mutagens. In particular, the mutagenesis by mutagens is preferred.

The more preferable microorganisms usable for the present invention are microorganisms containing reduced coenzyme $Q_{10}$ at a ratio of not less than 70 mole %, preferably not less than 75 mole %, more preferably not less than 80 mole %, still more preferably not less than 85 mole %, and particularly preferably not less than 90 mole %, among the entire coenzymes $Q_{10}$ in the case where the above-mentioned modified or improved microorganisms, preferably microorganisms mutated by mutagens, are evaluated by the above-mentioned proliferation method and the measurement method. In the fermentation production on the industrial scale, it is preferable to use microorganisms having a productivity of reduced coenzyme $Q_{10}$ per unit culture medium of not less than 1 μg/mL, preferably not less than 2 μg/mL, more preferably not less than 3 μg/mL, still more preferably not less than 5 μg/mL, particularly preferably not less than 10 μg/mL, much more preferably not less than 15 μg/mL, and most preferably not less than 20 μg/mL.

The mutagenesis may be carried out by a single mutagenesis; however, mutagenesis is preferably carried out not less than 2 times. That is because it was found that the productivity of reduced coenzyme $Q_{10}$ can be improved in the respective mutagenesis steps. It is needless to say that the candidates of the microbial cells to be mutated are, generally, those having a productivity of reduced coenzyme $Q_{10}$ as high as possible in the case where the evaluation is carried out by the above-mentioned proliferation method and measurement method.

The mutagenesis can be carried out by using optional and proper mutagens. The term "mutagen" encompasses, in a board definition, not only chemical agents having mutagenesis effects, for example, but also treatments such as UV radiation having mutagenesis effects. As examples of proper mutangens, there may be mentioned ethyl methanesulfonate, UV radiation, N-methyl-N'-nitro-N-nitrosoguanidine, nucleotide base analogues such as bromouracil, and acridines; however, they are not limited to these examples.

According to a conventional mutagenesis technique, successively to the mutagenesis, a proper selection of microbial cells having high productivity of reduced coenzyme $Q_{10}$ is carried out. For that, the culture obtained from a single colony should be evaluated, for example, by the above-mentioned proliferation method and measurement method. Since a reduced coenzyme $Q_{10}$ crystal forms a white solid layer or a colorless liquid phase, a productivity of reduced coenzyme $Q_{10}$ can be suitably evaluated by the above-mentioned measurement method at the time of selection of the colony.

In the processes of the present invention, high productivity of reduced coenzyme $Q_{10}$ in the fermentation production on the industrial scale can be achieved partially by using the microbial cells containing reduced coenzyme $Q_{10}$ at a ratio of not less than 70 mole % among the entire coenzymes $Q_{10}$ and, partially, by using the suitable conditions of culture (fermentation) for increasing a productivity of reduced coenzyme $Q_{10}$ per unit culture medium as described below. It is particularly preferable to combinedly use suitable microbial cells described above and the suitable conditions of culture (fermentation) as described below.

The culture is carried out, in general, in a culture medium containing major nutrients and micronutrients suited for microorganism proliferation. As the above-mentioned nutrients, there may be mentioned, for example, carbon sources (e.g. hydrocarbons such as glucose, sucrose, maltose, starch, corn syrup and molasses; alcohols such as methanol and ethanol), nitrogen sources (e.g. corn steep liquor, ammonium sulfate, ammonium phosphate, ammonium hydroxide, urea and peptone), phosphorus sources (e.g. ammonium phosphate and phosphoric acid) and micronutrients (e.g. minerals such as magnesium, potassium, zinc, copper, iron, manganese, molybdenum, sulfuric acid and hydrochloric acid; vitamins such as biotin, desthiobiotin and vitamin B1; amino acids such as alanine and histidine; and natural raw materials containing vitamins such as yeast extract and malt extract); however, these are not limitative ones, and commonly used ones may be used. Incidentally, in natural components of a culture medium, such as yeast extract, phosphorus sources such as phosphates are contained. The above-mentioned nutrients can be appropriately used in combination.

The culture is generally carried out at a temperature range of 15 to 45° C., preferably 20 to 37° C. If it is below 15° C., the proliferation speed of microorganisms tends to be too slow to allow the industrial production and at high temperatures exceeding 45° C., the viability of microorganisms tends to be easily hindered.

In general, the culture is carried out at a pH range of 4 to 9, preferably 5 to 8. If the pH is not more than 3 or not less than 10, proliferation of microorganisms tends to be easily inhibited.

In the fermentation production on the industrial scale, although it depends on the microorganism species, the concentration of the carbon sources (including the produced alcohols) during the culture is preferably controlled to a concentration that no adverse effects are substantially caused on the productivity of reduced coenzyme $Q_{10}$. Accordingly, it is preferable to control the culture so as to have the concentration of the carbon sources that no adverse effects are substantially caused on the productivity of reduced coenzyme $Q_{10}$, that is, generally to not more than 20 g/L, preferably not more than 5 g/L, and more preferably not more than 2 q/L in the broth.

To control the concentration of the carbon sources, a fed batch culture method is preferably used. The carbon source concentration in the broth can be controlled by adjusting the supply of nutrient sources (especially carbon sources) based on the culture control indexes such as pH, the dissolved oxygen concentration (DO) or the remaining saccharide concentration. Although it depends on the microorganism species, the supply of the nutrient sources may be started from the initial stage of the culture or during the culture. The supply of the nutrient sources may be continuous or intermittent. Incidentally, in supplying the nutrient sources, it is preferable to supply the above-mentioned carbon sources to the culture medium separately from other components.

The culture can be completed at the point when a desired amount of reduced coenzyme $Q_{10}$ is produced. The culture duration is not particularly limited and it is generally 20 to 200 hours.

The above-mentioned culture is generally carried out aerobically. The term "aerobically" means a condition that oxygen is supplied so as not to cause oxygen limitation (oxygen deficiency) during the culture, and preferably a condition that oxygen is supplied sufficiently so as not to cause substantial oxygen limitation during the culture. The culture is carried out generally under an aeration condition, preferably under an aeration and stirring condition.

By using the above-mentioned microorganisms and culture conditions, it becomes possible to obtain microbial cells containing reduced coenzyme $Q_{10}$ at a ratio of not less than 70 mole %, preferably not less than 75 mole % among the entire coenzymes $Q_{10}$. Furthermore, the productivity of reduced coenzyme $Q_{10}$ of as high as not less than 1 µg/mL, preferably not less than 2 µg/mL, and still more preferably not less than 3 µg/mL can be obtained.

Next, recovery of the reduced coenzyme $Q_{10}$ produced by the above-mentioned culture will be described.

In the present invention, an efficient production of reduced coenzyme $Q_{10}$ on the industrial scale is made to be possible partially by the above-mentioned suitable culture and partially by the suitable recovery process of reduced coenzyme $Q_{10}$ as described below.

Recovery of reduced coenzyme $Q_{10}$ is carried out by extraction from the microbial cells obtained by the above-mentioned culture using an organic solvent.

In the extraction, cells can be disrupted optionally. The cell disruption contributes to the efficient extraction of the reduced coenzyme $Q_{10}$ produced and accumulated in cells. It is needless to say that the cell disruption and extraction can be carried out at the same time.

Incidentally, "disruption" in the present invention may be carried out to the extent that the surface structure such as a cell wall is broken so as to make extraction of reduced coenzyme $Q_{10}$ possible; therefore, it is not necessary that microbial cells are torn or fragmentated.

The above-mentioned cell disruption is not necessarily required in the case of bacteria. However, in the case of yeast or fungi, the cell disruption is generally required and, when cells are not disrupted, it becomes difficult to efficiently recover the reduced coenzyme $Q_{10}$ produced and accumulated in the cells.

The above-mentioned disruption of microbial cells can be carried out by the following one or several disruption methods in optional order. As the disruption method, there may be mentioned, for example, a physical treatment, a chemical treatment, an enzymic treatment as well as a heating treatment, an autolysis, an osmolysis, a plasmoptysis and the like.

The above-mentioned physical treatment can be carried out, for example, by using a high pressure homogenizer, an ultrasonic homogenizer, a French press, a ball mill and the like or using them in combination.

The above-mentioned chemical treatment can be carried out, for example, by using an acid (preferably a strong acid) such as hydrochloric acid and sulfuric acid, a base (preferably a strong base) such ac sodium hydroxide and potassium hydroxide and the like or using them in combination.

The above-mentioned enzymic treatment can be carried out, for example, by using lysozyme, zymolyase, glucanase, Novozyme, protease, cellulase and the like or by using them appropriately in combination.

The above-mentioned heating treatment can be carried out, for example, by heating to the temperature range of 60 to 100° C. for about 30 minutes to 3 hours.

The above-mentioned autolysis can be carried out, for example, by treatment with a solvent such as ethyl acetate.

The osmolysis or the plasmoptysis for disrupting cells by treating cells with a solution having a different salt concentration from that in the cells are often combinedly used with the above-mentioned physical treatment, chemical treatment, enzymic treatment, heating treatment, autolysis and/or the like since the above lytic method alone is insufficient in the disruption effect.

As the cell disruption method as a pretreatment of extraction and recovery of reduced coenzyme $Q_{10}$, among the above-mentioned disruption methods, the physical treatment, the chemical treatment (particularly, an acid treatment and preferably the one with a strong acid (e.g. an acid having a pKa value of not more than 2.5 in the form of an aqueous solution) under the condition that reduced coenzyme $Q_{10}$ is protected from an oxidation reaction as described below) and the heating treatment are preferred. From the viewpoint of disruption efficiency, the physical treatment is more preferred.

A conventional cell disruption method and coenzyme $Q_{10}$ extraction method, specifically, a method comprising extracting coenzyme $Q_{10}$ by an organic solvent in the presence of sodium hydroxide and pyrogallol has problems in terms of cost, waste treatment, safety in effective utilization of waste microorganisms (waste cells) such as recovery of protein, and the like. However, the cell disruption method, particularly the physical treatment method of the present invention, does not cause subgeneration of a large quantity of salts by neutralization, and is a suitable method from a viewpoint of the waste treatment and the effective utilization of waste microorganisms (waste cells).

The form of the microbial cells to be used for the above-mentioned cell disruption may be a broth, a concentrated broth, microbial cells collected as wet cells from the broth, a product obtained by washing them, a suspension of the wet cells in a solvent (including, for example, water, physiological saline solution, buffers and the like), dry cells obtained by drying the above-mentioned wet cells, a suspension of the dry cells in a solvent (including, for example, water, physiological saline solution, buffers and the like), and the like. Preferred is an aqueous suspension of microbial cells, and in terms of operability and the like, more preferred are the broth, the concentrated broth, and the product obtained by washing them.

The form of the above-mentioned microbial cells or disrupted product thereof to be used for extraction and recovery of reduced coenzyme $Q_{10}$ is, similarly as described above, not particularly limited and may be wet cells/dry cells of the microbial cells/disrupted product thereof. Preferably, it is an aqueous suspension of the microbial cells or disrupted product thereof, and more preferably the broth, the concentrated and/or washed broth, or solutions obtained by disrupting them (each of them is an aqueous suspension).

The cell concentration in the above-mentioned suspension of the microbial cells or disrupted product thereof is not particularly limited and is generally 1 to 25% by weight on the basis of dry weight. Preferably, it is 10 to 20% by weight in terms of cost.

Reduced coenzyme $Q_{10}$ can be recovered by extracting the microbial cells and disrupted product thereof obtained in such a manner by an organic solvent.

As the organic solvent to be used for the extraction, there may be mentioned hydrocarbons, fatty acid esters, ethers, alcohols, fatty acids, ketones, nitrogen compounds (including nitriles and amides), sulfur compounds and the like.

Particularly, in extracting reduced coenzyme $Q_{10}$, in terms of protection from oxidation by a molecular oxygen, at least one species of hydrocarbons, fatty acid esters, ethers, and nitriles is preferably used. Among them, hydrocarbons and fatty acid esters are particularly preferable, and hydrocarbons are most preferable.

On the industrial production scale, complete oxygen elimination is very difficult to be achieved and, furthermore, fairly long periods of time are required for individual operations, unlike laboratory scale production, so that residual oxygen exerts a great adverse effect. The oxidation in question is directly connected to a subgeneration of oxidized coenzyme $Q_{10}$ from reduced coenzyme $Q_{10}$. Accordingly, use of the above-mentioned organic solvent (such as hydrocarbons, fatty acid esters, ethers, and nitriles) with high oxidation prevention effect in the extraction of reduced coenzyme $Q_{10}$ assists an efficient extraction.

The hydrocarbons are not particularly restricted, but there may be mentioned, for example, aliphatic hydrocarbons, aromatic hydrocarbons, halogenated hydrocarbons, and the like. Preferred are aliphatic hydrocarbons and aromatic hydrocarbons, and more preferred are aliphatic hydrocarbons.

The aliphatic hydrocarbons are not particularly restricted, and may be cyclic or acyclic, or saturated or unsaturated. However, generally, saturated ones are preferably used. Usually, ones containing 3 to 20 carbon atoms, preferably 5 to 12 carbon atoms, and more preferably 5 to 8 carbon atoms are used. As specific examples, there may be mentioned, for example, propane, butane, isobutane, pentane, 2-methylbutane, hexane, 2-methylpentane, 2,2-dimethylbutane, 2,3-dimethylbutane, heptane, heptane isomers (e.g. 2-methylhexane, 3-methylhexane, 2,3-dimethylpentane, 2,4-dimethylpentane), octane, 2,2,3-trimethylpentane, isooctane, nonane, 2,2,5-trimethylhexane, decane, dodecane, 2-pentene, 1-hexene, 1-heptene, 1-octene, 1-nonene, 1-decene, cyclopentane, methylcyclopentane, cyclohexane, methylcyclohexane, ethylcyclohexane, p-menthane, cyclohexene, and the like. Preferred are pentane, 2-methylbutane, hexane, 2-methylpentane, 2,2-dimethylbutane, 2,3-dimethylbutane, heptane, heptane isomers (e.g. 2-methylhexane, 3-methylhexane, 2,3-dimethylpentane, 2,4-dimethylpentane), octane, 2,2,3-trimethylpentane, isooctane, nonane, 2,2,5-trimethylhexane, decane, dodecane, cyclopentane, methylcyclopentane, cyclohexane, methylcyclohexane, ethylcyclohexane, p-menthane, and the like. More preferred are pentane, 2-methylbutane, hexane, 2-methylpentane, 2,2-dimethylbutane, 2,3-dimethylbutane, heptane, heptane isomers (e.g. 2-methylhexane, 3-methylhexane, 2,3-dimethylpentane, 2,4-dimethylpentane), octane, 2,2,3-trimethylpentane, isooctane, cyclopentane, methylcyclopentane, cyclohexane, methylcyclohexane, ethylcyclohexane, and the like.

Generally, heptanes, not only heptane but also heptane isomers such as methylcyclohexane having 7 carbon atoms and a mixture thereof are preferably used. More preferred are pentanes (e.g. pentane and the like) having 5 carbon atoms, hexanes (e.g. hexane, cyclohexane and the like) having 6 carbon atoms, and heptanes (e.g. heptane, methylcyclohexane and the like) having 7 carbon atoms. Particularly preferred are heptanes (e.g. heptane, methylcyclohexane and the like) in terms of especially high protection effect from oxidation, and the most preferred is heptane.

The aromatic hydrocarbons are not particularly restricted, but generally ones containing 6 to 20 carbon atoms, preferably 6 to 12 carbon atoms, and more preferably 7 to 10 carbon atoms are used. As specific examples, there may be mentioned, for example, benzene, toluene, xylene, o-xylene, m-xylene, p-xylene, ethylbenzene, cumene, mesitylene, tetralin, butylbenzene, p-cymene, cyclohexylbenzene, diethylbenzene, pentylbenzene, dipentylbenzene, dodecylbenzene, styrene, and the like. Preferred are toluene, xylene, o-xylene, m-xylene, p-xylene, ethylbenzene, cumene, mesitylene, tetralin, butylbenzene, p-cymene, cyclohexylbenzene, diethylbenzene, pentylbenzene and the like. More preferred are toulene, xylene, o-xylene, m-xylene, p-xylene, cumene, tetralin and the like, and most preferred is cumene.

The halogenated hydrocarbons are not particularly restricted, and may be cyclic or acyclic, or saturated or unsaturated. However, acyclic ones are preferably used in general. Usually, more preferred are chlorinated hydrocarbons and fluorinated hydrocarbons, and chlorinated hydrocarbons are still more preferred. Additionally, ones containing 1 to 6 carbon atoms, preferably 1 to 4 carbon atoms, and more preferably 1 to 2 carbon atoms are suitably used. As specific examples, for example, there may be mentioned dichloromethane, chloroform, carbon tetrachloride, 1,1-dichloroethane, 1,2-dichloroethane, 1,1,1-trichloroethane, 1,1,2-trichloroethane, 1,1,1,2-tetrachloroethane, 1,1,2,2-tetrachloroethane, pentachloroethane, hexachioroethane, 1,1-dichloroethylene, 1,2-dichloroethylene, trichloroethylene, tetrachloroethylene, 1,2-dichloropropane, 1,2,3-trichloropropane, chlorobenzene, 1,1,1,2-tetrafluoroethane, and the like. Preferred are dichloromethane, chloroform, carbon tetrachloride, 1,1-dichloroethane, 1,2-dichloroethane, 1,1,1-trichloroethane, 1,1,2-trichloroethane, 1,1-dichloroethylene, 1,2-dichloroethylene, trichloroethylene, chlorobenzene, 1,1,1,2-tetrafluoroethane, and the like. More preferred are dichloromethane, chloroform, 1,2-dichloroethylene, trichloroethylene, chlorobenzene, 1,1,1,2-tetrafluoroethane and the like.

The fatty acid esters are not particularly restricted, but there may be mentioned, for example, propionates, acetates, formates, and the like. Preferred are acetates and formates, and more preferred are acetates. Ester functional groups thereof are not particularly restricted, but, in general, preferred are alkyl esters having 1 to 8 carbon atoms and aralkyl esters having 7 to 12 carbon atoms, more preferred are alkyl esters having 1 to 6 carbon atoms, and still more preferred are alkyl esters having 1 to 4 carbon atoms.

As specific examples of the propionates, there may be mentioned, for example, methyl propionate, ethyl propionate, butyl propionate, isopentyl propionate, and the like. Preferred are ethyl propionate and the like.

As specific examples of the acetates, there may be mentioned, for example, methyl acetate, ethyl acetate, propyl acetate, isopropyl acetate, butyl acetate, isobutyl acetate, sec-butyl acetate, pentyl acetate, isopentyl acetate, sec-hexyl acetate, cyclohexyl acetate, benzyl acetate, and the like. Preferred are methyl acetate, ethyl acetate, propyl acetate, isopropyl acetate, butyl acetate, isobutyl acetate, sec-butyl acetate, pentyl acetate, isopentyl acetate, sec-hexyl acetate, cyclohexyl acetate, and the like. More preferred are methyl acetate, ethyl acetate, propyl acetate, isopropyl acetate, butyl acetate, isobutyl acetate, and the like. Most preferred is ethyl acetate.

As specific examples of the formates, there may be mentioned, for example, methyl formate, ethyl formate, propyl formate, isopropyl formate, butyl formate, isobutyl formate, sec-butyl formate, pentyl formate, and the like. Preferred are methyl formate, ethyl formate, propyl formate, butyl formate, isobutyl formate, pentyl formate, and the like. Most preferred is ethyl formate.

The ethers are not particularly restricted, and may be cyclic or acyclic, or saturated or unsaturated. But saturated ones are preferably used in general. Generally, ones containing 3 to 20 carbon atoms, preferably 4 to 12 carbon atoms and more preferably 4 to 8 carbon atoms are used. As specific examples, there may be mentioned, for example, diethyl ether, methyl tert-butyl ether, dipropyl ether, diisopropyl ether, dibutyl ether, dihexyl ether, ethyl vinyl ether, butyl vinyl ether, anisol, phenetole, butyl phenyl ether, methoxytoluene, dioxane, furan, 2-methylfuran, tetrahydrofuran, tetrahydropyran, ethylene glycol dimethyl ether, ethylene glycol diethyl ether, ethylene glycol dibutyl ether, ethylene glycol monomethyl ether, ethylene glycol monoethyl ether, ethylene glycol monobutyl ether, and the like. Preferred are diethyl ether, methyl tert-butyl ether, dipropyl ether, diisopropyl ether, dibutyl ether, dihexyl ether, anisol, phenetole, butyl phenyl ether, methoxytoluene, dioxane, 2-methylfuran, tetrahydrofuran, tetrahydropyran, ethylene glycol dimethyl ether, ethylene glycol diethyl ether, ethylene glycol dibutyl ether, ethylene glycol monomethyl ether, ethylene glycol monoethyl ether, and the like. More preferred are diethyl ether, methyl tert-butyl ether, anisol, dioxane, tetrahydrofuran, ethylene glycol monomethyl ether, ethylene glycol monoethyl ether, and the like. Still more preferred are diethyl ether, methyl test-butyl ether, anisol, and the like, and most preferred is methyl tert-butyl ether.

The alcohols are not particularly restricted but may be cyclic or acyclic, or saturated or unsaturated. Saturated ones are generally preferred, however. Generally, ones containing 1 to 20 carbon atoms, more preferably 1 to 12 carbon atoms, and still more preferably 1 to 6 carbon atoms are used. Among them, monohydric alcohols containing 1 to 5 carbon atoms, dihydric alcohols containing 2 to 5 carbon atoms, and trihydric alcohols containing 3 carbon atoms are preferred.

As specific examples of these alcohols, there may be mentioned, for example, monohydric alcohols such as methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, test-pentyl alcohol, 3-methyl-2-butanol, neopentyl alcohol, 1-hexanol, 2-methyl-1-pentanol, 4-methyl-2-pentanol, 2-ethyl-1-butanol, 1-heptanol, 2-heptanol, 3-heptanol, 1-octanol, 2-octanol, 2-ethyl-1-hexanol, 1-nonanol, 1-decanol, 1-undecanol, 1-dodecanol, allyl alcohol, propargyl alcohol, benzyl alcohol, cyclohexanol, 1-methylcyclohexanol, 2-methylcyclohexanol, 3-methylcyclohexanol, 4-methylcyclohexanol, and the like; dihydric alcohols such as 1,2-ethanediol, 1,2-propandiol, 1,3-propandiol, 1,2-butanediol, 1,3-butanediol, 1,4-butanediol, 2,3-butanediol, 1,5-pentanediol, and the like; and trihydric alcohols such as glycerol, and the like.

As the monohydric alcohols, preferred are methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, 1-heptanol, 2-heptanol, 3-heptanol, 1-octanol, 2-octanol, 2-ethyl-1-hexanol, 1-nonanol, 1-decanol, 1-undecanol, 1-dodecanol, benzyl alcohol, cyclohexanol, 1-methylcyclohexanol, 2-methylcyclohexanol, 3-methylcyclohexanol, 4-methylcyclohexanol, and the like. More preferred are methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, cyclohexanol, and the like. Still more preferred are methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, and the like. Particularly preferred are methanol, ethanol, 1-propanol, 2-propanol, 1-butanol, 2-butanol, isobutyl alcohol, 2-methyl-1-butanol, isopentyl alcohol, and the like. Most preferred is 2-propanol.

As the dihydric alcohols, preferred are 1,2-ethanediol, 1,2-propandiol, 1,3-propandiol, and the like. Most preferred is 1,2-ethanediol. As the trihydric alcohols, glycerol is preferred.

As fatty acids, there may be mentioned, for example, formic acid, acetic acid, propionic acid, and the like. Preferred are formic acid and acetic acid, and most preferred is acetic acid.

The ketones are not particularly restricted, and ones having 3 to 6 carbon atoms are preferably used. As specific examples, there may be mentioned, for example, acetone, methyl ethyl ketone, methyl butyl ketone, methyl isobutyl ketone, and the like. Preferred are acetone and methyl ethyl ketone, and most preferred is acetone.

The nitriles are not particularly restricted, and may be cyclic or acyclic, or saturated or unsaturated. However, saturated ones are preferably used in general. Generally, ones containing 2 to 20 carbon atoms, preferably 2 to 12 carbon atoms, and more preferably 2 to 8 carbon atoms are used.

As specific examples, there may be mentioned, for example, acetonitrile, propiononitrile, malononitrile, butyronitrile, isobutyronitrile, succinonitrile, valeronitrile, glutaronitrile, hexanenitrile, heptylcyanide, octylcyanide, undecanenitrile, dodecanenitrile, tridecanenitrile, pentadecanenitrile, stearonitrile, chloroacetonitrile, bromoacetonitrile, chloropropiononitrile, bromopropiononitrile, methoxyacetonitrile, methyl cyanoacetate, ethyl cyanoacetate, tolunitrile, benzonitrile, chlorobenzonitrile, bromobenzonitrile, cyanobenzoic acid, nitrobenzonitrile, anisonitrile, phthalonitrile, bromotolunitrile, methyl cyanobenzoate, methoxybenzonitrile, acetylbenzonitrile, naphthonitrile, biphenylcarbonitrile, phenylpropiononitrile, phenylbutyronitrile, methylphenylacetonitrile, diphenylacetonitrile, naphthylacetonitrile, nitrophenylacetonitrile, chlorobenzylcyanide, cyclopropanecarbonitrile, cyclohexanecarbonitrile, cycloheptanecarbonitrile, phenylcyclohexanecarbonitrile, tolylcyclohexanecarbonitrile, and the like.

Preferred are acetonitrile, propiononitrile, succinonitrile, butyronitrile, isobutyronitrile, valeronitrile, methyl cyanoacetate, ethyl cyanoacetate, benzonitrile, tolunitrile and chloropropiononitrile. More preferred are acetonitrile, propiononitrile, butyronitrile and isobutyronitrile, and most preferred is acetonitrile.

As the nitrogen compounds other than nitriles, there may be mentioned, for example, amides such as formamide, N-methylformamide, N,N-dimethylformamide, N,N-dimethylacetoamide, N-methylpyrrolidone, and nitromethane, triethylamine, pyridine, and the like.

As the sulfur compounds, there may be mentioned, for example, dimethyl sulfoxide, sulfolane, and the like.

In selecting the organic solvent to be used from among the organic solvents mentioned above, such properties as boiling point and viscosity (e.g. the solvent should have a boiling point which allows appropriate warming for increasing solubility and facilitates a solvent removal from wet masses by drying and solvent recovery from crystallization filtrates and the like (about 30 to 150° C. at 1 atm), a melting point such that solidification hardly occurs in handling at room temperature as well as upon cooling to room temperature or below (not lower than about 0° C., preferably not lower than about 10° C., more preferably not lower than about 20° C.), and a low viscosity (not higher than about 10 cp at 20° C. and the like)) are preferably taken into consideration.

The oxidation prevention effect on reduced coenzyme $Q_{10}$ in a solvent tends to increase in a highly-concentrated solution of reduced coenzyme $Q_{10}$. Reduced coenzyme $Q_{10}$ shows high solubility in the above-mentioned organic solvents with high oxidation prevention effect (e.g. hydrocarbons, fatty acid esters and the like). The high solubility makes it possible to handle the highly-concentrated solution and to promote the oxidation prevention. A preferable concentration of reduced coenzyme $Q_{10}$ for oxidation prevention at the time of extraction is not particularly limited, but is generally not less than 0.001% by weight, preferably not less than 0.01% by weight, and more preferably not less than 0.1% by weight as the concentration of reduced coenzyme $Q_{10}$ in the above-mentioned organic solvent. The upper limit is not particularly limited, however, in general, it is not more than 10% by weight.

Among the above-mentioned organic solvents, to extract and recover reduced coenzyme $Q_{10}$ from wet cells and dry cells of the microbial cells or disrupted product thereof, hydrophilic organic solvents are preferably used. Specifically, there may be mentioned acetone, acetonitrile, methanol, ethanol, 1-propanol, 2-propanol and the like.

Furthermore, among the above-mentioned organic solvents, to extract and recover reduced coenzyme $Q_{10}$ from the aqueous suspension of the microbial cells or disrupted product thereof, hydrophobic organic solvents are preferably used. Use of such solvents assists the removal of water-soluble substances derived from microorganisms. Many of hydrophobic organic solvents have high oxidation prevention effect as described above, thus are very advantageous.

As the hydrophobic organic solvents, hydrocarbons, fatty acid esters and ethers are preferred.

In the case of the above-mentioned extraction operation, when reduced coenzyme $Q_{10}$ is extracted from the aqueous suspension of the microbial cells or disrupted product thereof, particularly from the aqueous suspension of the disrupted product, further particularly the case in which the disrupted product is physically treated, by an organic solvent, emulsions tend to be partly formed because of the presence of cell components such as proteins and phase separation tends to be difficult. Therefore, it becomes important to suppress the formation of emulsions mentioned above and to efficiently carry out extraction.

For that, as an extraction solvent, in addition to the above-mentioned hydrophobic organic solvent, it is preferable to use a hydrophilic organic solvent as an auxiliary solvent in combination.

In this case, the hydrophobic organic solvent is not particularly limited and those mentioned above may be used. Preferred are hydrocarbons, and more preferred are aliphatic hydrocarbons. Among the aliphatic hydrocarbons, those having 5 to 8 carbon atoms are preferably used.

As specific examples of the aliphatic hydrocarbons containing 5 to 8 carbon atoms, there may be mentioned, for example, pentane, 2-methylbutane, hexane, 2-methylpentane, 2,2-dimethylbutane, 2,3-dimethylbutane, heptane, heptane isomers (e.g. 2-methylhexane, 3-methylhexane, 2,3-dimethylpentane, 2,4-dimethylpentane), octane, 2,2,3-trimethylpentane, isooctane, cyclopentane, methylcyclopentane, cyclohexane, methylcyclohexane, ethylcyclohexane, and the like. Particularly preferred are hexane, heptane and methylcyclohexane, and most preferred are hexane and heptane.

The hydrophilic organic solvent to be used in combination with the above-mentioned hydrophobic organic solvent is not particularly limited and those mentioned above may be used. Preferred are alcohols. Among the alcohols, monohydric alcohols having 1 to 5 carbon atoms are preferably used. As specific examples thereof, there may be mentioned, for example, methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, and the like. Particularly preferred are methanol, ethanol, 1-propanol and 2-propanol, and most preferred is 2-propanol.

The amounts of the above-mentioned hydrophilic organic solvent and hydrophobic organic solvent to be used are not particularly limited. But preferably, as the organic solvent is used in a range of 5 to 50% by volume and the hydrophobic organic solvent is used in a range of 25 to 65% by volume relative to the total volume of the entire solution.

In recovering reduced coenzyme $Q_{10}$, the temperature at the time of extraction is not particularly limited and is generally in a range of 0 to 60° C. and preferably 20 to 50° C.

As the extraction method, both batch extraction and continuous extraction (preferably countercurrent multistage extraction) may be used. However, the continuous extraction (preferably countercurrent multistage extraction) is preferable in terms of productivity. The stirring duration in the batch extraction is not particularly limited but is generally not less than 5 minutes. The average retention time in the continuous extraction is not particularly limited but is generally not less than 10 minutes.

In recovering reduced coenzyme $Q_{10}$, it is preferable to be careful so that reduced coenzyme $Q_{10}$ is not decomposed (e.g. so that reduced coenzyme $Q_{10}$ is not oxidized to oxidized coenzyme $Q_{10}$). For that, the above-mentioned extraction (including cell disruption) is preferably carried out under an acidic to a weakly basic condition, and more preferably under an acidic to a neutral condition. In the case where a pH is used as an index, although it depends on the contact time, the pH is generally not more than 10, preferably not more than 9, more preferably not more than 8, and still more preferably not more than 7.

By the above-mentioned conditions, an oxidation reaction can be substantially prevented and, optionally, more strictly, the above-mentioned cell disruption and/or extraction are preferably carried out under the condition that reduced coenzyme $Q_{10}$ is protected from an oxidation reaction. It is preferable to carry out at least the extraction under this condition, and it is more preferable to carry out the disruption and the extraction under this condition.

As "the condition that reduced coenzyme $Q_{10}$ is protected from an oxidation reaction" means, for example, a deoxygenized atmosphere (an atmosphere of an inert gas such as nitrogen gas, carbon dioxide gas, helium gas, argon gas or hydrogen gas, reduced pressure, a boiling condition); a high salt concentration condition, for example, preferably a condition where salts (e.g. inorganic salts such as sodium chloride and sodium sulfate) are contained in not less than about 5% in an aqueous phase; the condition in the presence of a strong acid (e.g. an acid with a pKa value of not more than 2.5 in an aqueous solution), for example, in the presence of not less than 0.1 mole % of the strong acid relative to 1 mole of reduced coenzyme $Q_{10}$; and the condition in the presence of an antioxidant, for example, in the concomitant presence of ascorbic acid, citric acid, salts and esters thereof (e.g. not less than 0.1% by weight of them relative to reduced coenzyme $Q_{10}$). There may also be mentioned a reduction condition (a condition in which oxidized coenzyme $Q_{10}$ can be converted into reduced coenzyme $Q_{10}$), for example, a condition involving a contact with a reducing agent such as dithionous acid.

By the above-mentioned culture (fermentation) and extraction, reduced coenzyme $Q_{10}$ can be suitably produced and recovered. Preferably, an extract containing not less than 70 mole %, preferably not less than 75 mole % of reduced coenzyme $Q_{10}$ among the entire coenzymes $Q_{10}$ is obtained.

Thus-obtained extract containing reduced coenzyme $Q_{10}$ is optionally purified by column chromatography, reduction treatment, or the like and then subjected to crystallization to obtain high-purity reduced coenzyme $Q_{10}$ crystals. Incidentally, also in this case, a series of treatment steps are preferably carried out under "the condition that reduced coenzyme $Q_{10}$ is protected from an oxidation reaction" mentioned above.

In the present invention, oxidized coenzyme $Q_{10}$ can be produced by oxidizing the above-mentioned microbial cells or disrupted product thereof and then extracting oxidized coenzyme $Q_{10}$ by an organic solvent, or extracting reduced coenzyme $Q_{10}$ from the microbial cells or disrupted product thereof by an organic solvent, purifying optionally and oxidizing the resultant to oxidized coenzyme $Q_{10}$.

The above-mentioned oxidation may be carried out by, for example, mixing reduced coenzyme $Q_{10}$ (preferably an aqueous suspension of the microbial cells or disrupted product thereof containing reduced coenzyme $Q_{10}$, an extract containing reduced coenzyme $Q_{10}$ or the like) with an oxidizing agent (e.g. manganese dioxide or the like) and then, for example, oxidizing the mixture at room temperature (e.g. 30° C.) for not less than 30 minutes. In the case where the microbial cells or disrupted product thereof are oxidized, the extraction operation of oxidized coenzyme $Q_{10}$ can be carried out in the same manner as the above-mentioned extraction operation of reduced coenzyme $Q_{10}$. Thereby, oxidized coenzyme $Q_{10}$ can be efficiently recovered. Incidentally, it is not necessary to carry out the recovery of oxidized coenzyme $Q_{10}$ under "the condition that reduced coenzyme $Q_{10}$ is protected from an oxidation reaction", which is recommended for the recovery of reduced coenzyme $Q_{10}$ and the recovery may be carried out in consideration of general safe operation and the like. The thus-obtained oxidized coenzyme $Q_{10}$ may be optionally purified by column chromatography or the like, and, finally by conducting crystallization operation, high-purity oxidized coenzyme $Q_{10}$ crystals may be obtained.

BRIEF DESCRIPTION OF THE DRAWINGS

FIG. 1 shows a schematic diagram of a countercurrent 3-step continuous extraction apparatus used in Example 8.

BEST MODE FOR CARRYING OUT THE INVENTION

The following examples illustrate the present invention in further detail. These examples are, however, by no means limitative of the scope of the present invention.

EXAMPLE 1

Various coenzyme $Q_{10}$-producing microorganisms shown in the following Tables 1 to 3 were cultured with shaking (amplitude: 2 cm, 310 reciprocation/min) at 25° C. for 72 hours in 10 mL of culture media [(glucose: 20 g, peptone: 5 g, yeast extract: 3 g, malt extract: 3 g)/L, pH: 6.0] using test tubes (inner diameter: 21 mm, entire length: 200 mm), and the obtained broth were optionally concentrated. Under a nitrogen atmosphere, in the concomitant presence of 3 parts by volume of isopropanol and 18.5 parts by volume of n-hexane relative to 10 parts by volume of the broth, the obtained solutions were vigorously shaken for 3 minutes using 10 parts by volume of glass beads (425 to 600 µm) to carry out cell disruption and extraction. The obtained hexane phases were evaporated (at 40° C.) under reduced pressure and analyzed by high performance liquid chromatography (HPLC) to determine the ratio and the production amount of reduced coenzyme $Q_{10}$.

HPLC Conditions

Column: YMC-Pack 4.6×250 mm (manufactured by YMC. Co., Ltd.)

Mobile phase: methanol/n-hexane=85/15

Flow rate: 1 mL/min

Detection: UV 275 nm

The results are shown in Tables 1 to 3. The ratio of reduced coenzyme $Q_{10}$ means a mole percentage value of the ratio of reduced coenzyme $Q_{10}$ relative to the total of oxidized coenzyme $Q_{10}$ and reduced coenzyme $Q_{10}$ on the basis of the areas of the peaks of reduced coenzyme $Q_{10}$ and oxidized coenzyme $Q_{10}$ and the ratio of the mole absorption coefficients thereof (1:7.5).

TABLE 1

| Strain name | Upper stand: Ratio of reduced coenzyme Q10 (%)<br>Lower stand: Production amount of reduced coenzyme Q10 (µg/ml) |
|---|---|
| *Agrobacterium tumefacience* IFO 13263 | 82 |
| | 7 |
| *Agrobacterium radiobacter* ATCC 4718 | 78 |
| | 7 |
| *Aspergillus clavatus* JCM 1718 | 83 |
| | 2 |
| *Acetobacter xylinum* IFO15237 | 77 |
| | 2 |
| *Aminobacter aganouensis* JCM 7854 | 70 |
| | 3 |
| *Agromonas oligotrophica* JCM 1494 | 75 |
| | 2 |
| *Acidiphilium multivorum* JCM 8867 | 73 |
| | 3 |
| *Bulleromyces albus* IFO 1192 | 72 |
| | 2 |
| *Bullera armeniaca* IFO 10112 | 85 |
| | 7 |
| *Brevundimonas diminuta* JCM 2788 | 82 |
| | 5 |
| *Cryptococcus laurentii* IFO 0609 | 79 |
| | 6 |
| *Chionosphaera apobasidialis* CBS 7430 | 71 |
| | 2 |
| *Candida curvata* ATCC 10567 | 74 |
| | 3 |
| *Cerinosterus luteoalbus* JCM 2923 | 79 |
| | 5 |
| *Exisophiala alcalophila* JCM12519 | 77 |
| | 3 |
| *Exobasidium gracile* IFO7788 | 79 |
| | 2 |
| *Fellomyces fuzhouensis* IFO 10374 | 70 |
| | 2 |
| *Filobasidiella neoformans* CBS 132 | 88 |
| | 2 |
| *Filobasidium capsuloigenum* CBS 1906 | 82 |
| | 3 |
| *Geotrichum capitatum* JCM 6258 | 77 |
| | 3 |
| *Graphiola cylindrica* IFO 6426 | 75 |
| | 4 |
| *Gluconobacter suboxydans* IFO 3257 | 86 |
| | 6 |
| *Kockovaella imperatae* JCM 7826 | 78 |
| | 2 |

TABLE 2

| Strain name | Upper stand: Ratio of reduced coenzyme Q10 (%) / Lower stand: Production amount of reduced coenzyme Q10 (μg/ml) |
|---|---|
| Kurtzmanomyces nectairei IFO 10118 | 79 / 2 |
| Lalaria cerasi CBS 275.28 | 75 / 2 |
| Leucosporidium scottii IFO 1212 | 88 / 6 |
| Legionella anisa JCM 7573 | 73 / 3 |
| Methylobacterium extorguens JCM 2802 | 72 / 2 |
| Mycoplana ramosa JCM 7822 | 80 / 2 |
| Oosporidium margaritiferum CBS2531 | 76 / 2 |
| Pseudomonas denitrificans IAM 12023 | 85 / 8 |
| Pseudomonas shuylkilliensis IAM 1092 | 84 / 6 |
| Psedozyma aphidis CBS 517.23 | 79 / 5 |
| Paracoccus denitrificans JCM 6892 | 83 / 5 |
| Petromyces alliaceus IFO 7530 | 72 / 2 |
| Rhodotorula glutinis IFO 1125 | 79 / 7 |
| Rhodotorula minuta IFO 0387 | 74 / 8 |
| Rhodosporidium diobovatum ATCC 1830 | 86 / 4 |
| Rhizomonas suberifaciens IFO 15212 | 82 / 2 |
| Rhodobium orients JCM 9337 | 80 / 2 |
| Rhodoplanes elegans JCM9224 | 74 / 2 |
| Rhodopseudomonas palustris JCM2524 | 90 / 6 |
| Rhodobacter capsulatus SB 1003 | 95 / 6 |
| Sporobolomyces holsaticus IFO 1034 | 72 / 9 |
| Sporobolomyces pararoseus IFO 0471 | 93 / 8 |
| Sporidiobolus johnsonii IFO 1840 | 73 / 7 |
| Saitoella complicata IFO 10748 | 97 / 9 |

TABLE 3

| Strain name | Upper stand: Ratio of reduced coenzyme Q10 (%) / Lower stand: Production amount of reduced coenzyme Q10 (μg/ml) |
|---|---|
| Schizosaccharomyces pombe IFO 0347 | 90 / 8 |
| Sphingomonas parapaucimobilis IFO 15100 | 78 / 7 |
| Sporotrichum cellulophilium ATCC 20493 | 73 / 6 |
| Sympodiomycopsis paphiopedili JCM 8318 | 80 / 6 |
| Sterigmatosporidium polymorphum IFO 10121 | 72 / 2 |
| Sphingomonas adhesiva JCM 7370 | 80 / 3 |
| Tapharina caerulescens CBS 351.35 | 81 / 2 |
| Tremella mesenterica ATCC 24438 | 89 / 3 |
| Trichosporon cutaneum IFO 1198 | 95 / 8 |
| Tilletiaria anomala CBS 436.72 | 75 / 4 |
| Tilletia caries JCM 1761 | 80 / 3 |
| Tolyposporium bullatum JCM 2006 | 73 / 4 |
| Tilletiopsis washintonesis CBS 544 | 76 / 2 |
| Ustilago esculenta IFO 9887 | 78 / 2 |
| Udeniomyces megalosporus JCM 5269 | 87 / 2 |
| Xanthophilomyces dendrorhous IFO 10129 | 84 / 2 |
| Xanthobacter flavus JCM1204 | 80 / 2 |
| Paecilomyces lilacinus ATCC10114 | 80 / 5 |
| Acremonium chrysogenum ATCC11550 | 75 / 5 |
| Hyphomonas hirschiana ATCC33886 | 72 / 3 |
| Rhizobium meliloti ATCC9930 | 85 / 10 |

EXAMPLE 2

Rhodotorula glutinis IFO1125 was aerobically cultured at 25° C. for 48 hours in a culture medium (peptone: 5 g, yeast extract: 3 g, malt extract: 3 g, glucose: 20 g/L, pH: 6.0). The cells after the culture were collected by centrifugation and suspended in a phosphoric acid buffer solution at pH 7 to which N-methyl-N -nitro-N-nitrosoguanidine have been added so as to have its concentration of 200 μg/mL. After maintaining the solution at 25° C. for 1 hour, the cells were washed for 5 times with a 0.9% NaCl solution and further suspended in a 0.9% NaCl solution. The obtained cell suspension was properly diluted and a colony was to be formed on an agar plate of the above-mentioned culture medium. The production amount and the ratio of reduced coenzyme $Q_{10}$ in the isolated mutant strain were determined in the same manner as Example 1. The strains having higher production amount and the ratio of reduced coenzyme $Q_{10}$ as compared with those of wild strains was further mutated repeatedly. As the result, by repeating the mutagenesis for 10 times, mutant strains with productivity of not less than 15 μg/mL were obtained. In this case, the ratio of reduced coenzyme $Q_{10}$ was not less than 80 mole %.

EXAMPLE 3

Saitoella complicata IFO 10748 was aerobically cultured at 25° C. for 72 hours in 10 L of a culture medium (peptone: 5 g, yeast extract: 3 g, malt extract: 3 g, glucose: 20 g/L, pH: 6.0). The obtained cells were disrupted for 2 times at 80 MPa of disruption pressure by a pressure homogenizer (manufactured by Lanni Co.) sealed with nitrogen gas to obtain a cell-disrupted solution. The cell-disrupted solution was subjected to extraction with 30 parts by volume of isopropanol and 40 parts by volume of hexane for 3 times to obtain an extract. The extraction ratio was 99%. The ratio of reduced coenzyme $Q_{10}$ was 97 mole %.

EXAMPLE 4

When mutant strains of *Rhodotorula glutinis* IFO1125 were aerobically cultured at 25° C. in 10 L of a culture medium (peptone: 10 g, yeast extract: 5 g, malt extract: 3 g, glucose: 20 g/L, pH: 6.0), glucose was fed at the rate of 4 g/h after the lapse of 48 hours to 96 hours (fed glucose amount: 190 g). The production amount of reduced coenzyme $Q_{10}$ per culture medium was not less than 20 µg/mL and the ratio of reduced coenzyme $Q_{10}$ was not less than 80 mole %.

EXAMPLE 5

The extract obtained in Example 3 was subjected to solvent substitution with a hexane solution, the resultant was adsorbed in a column filled with silica gel and subjected to development and elution by a solution of n-hexane/diethyl ether (9/1) to obtain a fraction containing reduced coenzyme $Q_{10}$. Furthermore, the fraction was cooled to 2° C. with stirring to obtain a white slurry. All the above-mentioned operations were carried out in a nitrogen atmosphere. The obtained slurry was filtered under reduced pressure, the resulting wet crystals were washed with the development solution same as used above (the temperature of the solvent used for washing was 2° C.), and the wet crystals were dried under reduced pressure (20 to 40° C., 1 to 30 mmHg) to obtain 81 mg of white dry crystals. The purity of the obtained crystals was 99.90 and the ratio of reduced coenzyme $Q_{10}$ was 90 mole %.

EXAMPLE 6

The extract obtained in Example 3 was subjected to solvent substitution with n-hexane the resultant was added with 50 mg of manganese dioxide, and the mixture was stirred at 30° C. for 30 minutes. Thus-obtained reaction solution was fractionated and purified in the same manner as Example 5 to obtain 74 mg of high-purity oxidized coenzyme $Q_{10}$.

EXAMPLE 7

*Saitoella complicata* IFO 10748 was aerobically cultured at 25° C. for 72 hours in 500 mL of a culture medium (peptone: 5 g, yeast extract: 3 g, malt extract: 3 g, glucose: 20 g/L, pH: 6.0). The obtained cells were disrupted for 2 times at 80 MPa of disruption pressure by a pressure homogenizer (manufactured by Lanni Co.) sealed with nitrogen gas to obtain a cell-disrupted solution. The ratio of reduced coenzyme $Q_{10}$ in the cell-disrupted solution was 97% relative to the entire coenzymes $Q_{10}$ including oxidized coenzyme $Q_{10}$. 200 mL of the cell-disrupted solution was mixed with isopropanol and n-hexane at the ratios shown in the first extraction section in the following Table 4 so as to adjust the total solvent amount to be 500 mL and the mixtures were stirred at 40° C. for 30 minutes to carry out the first extraction. After completion of the extraction, the resultants were kept standing for 10 minutes and the separated upper layers were collected. The volume ratios of the lower layers (residues) relative to the total solution amounts were defined as indexes of separability and shown as the interface positions in Table 4.

Furthermore, in order to carry out the second extraction, the solvent concentrations of the residual layers were measured and isopropanol and hexane were further added so as to keep the solvent ratios in the entire solutions be the ratios shown in the second extraction section in Table 4. The resulting solutions were stirred at 40° C. for 30 minutes. Then, the solutions were kept standing for 10 minutes and the upper layers were collected in the same manner as described above to determine the solvent concentrations of the residual layers. Isopropanol and hexane were added thereto so as to keep the solvent ratios in the entire solutions be the ratios shown in the third extraction section in Table 4, and the solutions were stirred at 25° C. for 30 minutes to carry out the third extraction.

The ratios of the amounts of reduced coenzyme $Q_{10}$ contained in the collected upper layers of each of the first, second and third steps relative to the amount of reduced coenzyme $Q_{10}$ contained in the cell-disrupted solution or the extraction residue before the extraction were defined as the extraction ratios of reduced coenzyme $Q_{10}$ in the respective steps. The calculation results are shown in Table 4. The integrated extraction ratios of reduced coenzyme $Q_{10}$ in the second and third extraction steps are also shown. In any steps, the static separability was excellent and the integrated extraction ratio in the case where extraction was repeated for 3 times was as high as not less than 90% to show high recovery ratio. Particularly, in the case where the isopropanol concentration was adjusted to be not less than 30%, the recovery ratio was as high as not less than 99%.

TABLE 4

| | | Solvent ratio (vol %) | | | Extraction ratio (%) | |
|---|---|---|---|---|---|---|
| | | Isopropanol | Hexane | Interface position | Respective extraction ratio | Integrated extraction ratio |
| Case1 | First | 18.8 | 52.7 | 0.492 | 73.6 | 73.6 |
| | Second | 19.0 | 52.4 | 0.624 | 47.6 | 86.2 |
| | Third | 29.7 | 41.7 | 0.645 | 55.5 | 93.8 |
| Case2 | First | 31.3 | 40.2 | 0.499 | 90.7 | 90.7 |
| | Second | 37.7 | 33.7 | 0.549 | 83.7 | 98.5 |
| | Third | 40.6 | 30.9 | 0.565 | 40.1 | 99.1 |
| Case3 | First | 31.3 | 40.2 | 0.526 | 89.0 | 89.0 |
| | Second | 34.1 | 37.3 | 0.553 | 85.8 | 98.3 |
| | Third | 36.8 | 34.6 | 0.555 | 46.6 | 99.1 |
| Case4 | First | 31.3 | 40.2 | 0.526 | 89.0 | 89.0 |
| | Second | 34.1 | 37.3 | 0.553 | 85.8 | 98.3 |
| | Third | 42.4 | 29.0 | 0.644 | 50.0 | 99.0 |
| Case5 | First | 31.3 | 40.2 | 0.526 | 89.0 | 89.0 |
| | Second | 40.1 | 31.4 | 0.595 | 88.1 | 98.6 |
| | Third | 40.7 | 30.7 | 0.593 | 45.3 | 99.1 |
| Case6 | First | 31.3 | 40.2 | 0.526 | 89.0 | 89.0 |
| | Second | 40.1 | 31.4 | 0.595 | 88.1 | 98.6 |
| | Third | 45.8 | 25.7 | 0.663 | 40.7 | 99.0 |

EXAMPLE 8

*Saitoella complicata* IFO 10748 was aerobically cultured at 25° C. for 72 hours in 750 L of a culture medium (peptone: 5 g, yeast extract: 3 g, malt extract: 3 g, glucose: 20 g/L, pH: 6.0). The obtained cells were disrupted for 2 times at 140 MPa of disruption pressure by a pressure homogenizer (manufactured by Lanni Co.) sealed with nitrogen gas to obtain a cell-disrupted solution. The cell-disrupted solution was subjected to continuous extraction by a countercurrent 3-step continuous extraction apparatus shown in FIG. 1. The capacity of the stirring tank was 630 L and the capacity of the static separation tank was 200 L. The cell-disrupted solution was supplied to the first stirring tank and isopropanol and n-hexane were supplied to respective steps. The supply amount of the cell-disrupted solution was 2 L/min and the supply amounts of isopropanol and n-hexane were adjusted to be 1.3

L/min for isopropanol and 3.7 L/min for n-hexane as the total of the supply amounts in respective steps. In this case, the solvent concentration in respective steps was properly adjusted so that the isopropanol concentration of 5 to 50 v/v % and the n-hexane concentration of 25 to 65 v/v % were kept. The extraction temperature was 40° C. and the treatment duration was 6 hours. At the point after the lapse of 6 hours, the recovery ratio of reduced coenzyme $Q_{10}$ extracted from the cell-disrupted solution was calculated on the basis of reduced coenzyme $Q_{10}$ remaining in the extraction residue in the static separation tank in the third step to find the recovery ratio of 98.9%. The static separation was well carried out during the entire operation period and stable continuous extraction was possible.

INDUSTRIAL APPLICABILITY

According to the processes of the present invention, reduced coenzyme $Q_{10}$ can be produced cheaply on the industrial scale by considerably simple steps comprising culturing microorganisms and recovering reduced coenzyme $Q_{10}$. In addition, oxidized coenzyme $Q_{10}$ can also be produced by simple processes.

The invention claimed is:
1. A process for producing the reduced coenzyme $Q_{10}$ represented by the following formula (I):

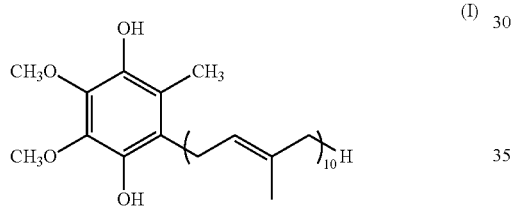

which comprises culturing reduced coenzyme $Q_{10}$-producing microorganisms in a culture medium containing a carbon source, a nitrogen source, a phosphorus source and a micronutrient to obtain microbial cells containing reduced coenzyme $Q_{10}$ at a ratio of not less than 70 mole % among the entire coenzymes $Q_{10}$, and extracting the reduced coenzyme $Q_{10}$ by an organic solvent under the condition that the reduced coenzyme $Q_{10}$ is protected from an oxidation reaction, to thereby obtain an extract containing not less than 70 mole % reduced coenzyme $Q_{10}$ among the entire coenzymes $Q_{10}$, and
wherein the condition that the reduced coenzyme $Q_{10}$ is protected from an oxidation reaction is selected from the group consisting of an atmosphere of inert gas, a high salt concentration condition where inorganic salts are contained in not less than about 5% in an aqueous phase, the condition in the presence of not less than 0.1 mole % of a strong acid with a pKa value of not more than 2.5 relative to 1 mole of reduced coenzyme $Q_{10}$, the condition in the presence of ascorbic acid, citric acid or salts and esters thereof, and the condition in the presence of dithionous acid.
2. The process according to claim 1, wherein the culture is carried out at 15 to 45° C. and at a pH of 4 to 9.
3. The process according to claim 1,
wherein the concentration of the carbon source in the culture is controlled to a concentration that no adverse effects are substantially caused on the productivity of reduced coenzyme $Q_{10}$.
4. The process according to claim 1,
wherein the extraction of reduced coenzymes $Q_{10}$ is carried out from wet cells or dry cells of the microbial cells or disrupted product thereof by using a hydrophilic organic solvent.
5. The process according to claim 1,
wherein the extraction of the reduced coenzymes $Q_{10}$ is carried out from an aqueous suspension of the microbial cells or disrupted product thereof by using a hydrophobic organic solvent.
6. The process according to claim 5,
wherein the hydrophobic organic solvent is a hydrocarbon, a fatty acid ester or an ether.
7. The process according to claim 5,
wherein the hydrophilic organic solvent is used as an auxiliary solvent in combination with the hydrophobic organic solvent.
8. The process according to claim 7,
wherein the hydrophobic organic solvent is a hydrocarbon, and the hydrophilic organic solvent is an alcohol.
9. The process according to claim 7,
wherein the extraction is carried out under the condition that the hydrophobic organic solvent is contained in 25 to 65% by volume and the hydrophilic organic solvent is contained in 5 to 50% by volume.
10. The process according to claim 1,
wherein the reduced coenzyme $Q_{10}$-producing microorganisms have not less than 1 μg/mL of a productivity of reduced coenzyme $Q_{10}$ per unit culture medium when measured by HPLC.
11. The process according to claim 10,
wherein the microorganisms are microorganisms of the genus *Agrobacterium*, the genus *Aspergillus*, the genus *Acetobacter*, the genus *Aminobacter*, the genus *Agromonas*, the genus *Acidiphilium*, the genus *Bulleromyces*, the genus *Bullera*, the genus *Brevundimonas*, the genus *Cryptococcus*, the genus *Chionosphaera*, the genus Candida, the genus *Cerinosterus*, the genus *Exisophiala*, the genus *Exobasidium*, the genus *Fellomyces*, the genus *Filobasidiella*, the genus *Filobasidium*, the genus *Geotrichum*, the genus *Graphiola*, the genus *Gluconobacter*, the genus *Kockovaella*, the genus *Kurtzmanomyces*, the genus *Lalaria*, the genus *Leucosporidium*, the genus *Legionella*, the genus *Methylobacterium*, the genus *Mycoplana*, the genus *Oosporidium*, the genus *Pseudomonas*, the genus *Psedozyma*, the genus *Paracoccus*, the genus *Petromyces*, the genus *Rhodotorula*, the genus *Rhodosporidium*, the genus *Rhizomonas*, the genus *Rhodobium*, the genus *Rhodoplanes*, the genus *Rhodopseudomonas*, the genus *Rhodobacter*, the genus *Sporobolomyces*, the genus *Sporidiobolus*, the genus *Saitoella*, the genus *Schizosaccharomyces*, the genus *Sphingomonas*, the genus *Sporotrichum*, the genus *Sympodiomycopsis*, the genus *Sterigmatosporidium*, the genus *Tapharina*, the genus *Tremella*, the genus *Trichosporon*, the genus *Tilletiaria*, the genus *Tilletia*, the genus *Tolyposporium*, the genus *Tilletiopsis*, the genus *Ustilago*, the genus *Udeniomyces*, the genus *Xanthophilomyces*, the genus *Xanthobacter*, the genus *Paecilomyces*, the genus *Acremonium*, the genus *Hyhomonus*, or the genus *Rhizobium*.
12. The process according to claim 1,
wherein the production amount of reduced coenzyme $Q_{10}$ on completion of the culture is not less than 1 μg/mL.
13. The process according to claim 3,
wherein the culture is carried out by a fed batch culture method.

14. The process according to claim 13,
wherein the carbon source is supplied to the culture medium separately from other components.

15. The process according to claim 1,
wherein, as the organic solvent to be used for extraction of reduced coenzyme $Q_{10}$, at least one species of hydrocarbons, fatty acid esters, ethers and nitriles is used.

16. The process according to claim 4,
wherein the hydrophilic organic solvent is acetone, acetonitrile, methanol, ethanol, 1-propanol or 2-propanol.

17. The process according to claim 7,
wherein the hydrophobic organic solvent is an aliphatic hydrocarbon, and the hydrophilic organic solvent is a monohydric alcohol containing 1 to 5 carbon atoms.

18. The process according to claim 7,
wherein the hydrophobic organic solvent is at least one species of hexane and heptane, and the hydrophilic organic solvent is at least one species of methanol, ethanol, 1-propanol and 2-propanol.

19. The process according to claim 5,
wherein the extraction is carried out by continuous extraction.

20. The process according to claim 1,
wherein the obtained reduced coenzyme $Q_{10}$ is purified optionally and crystallized to obtain a reduced coenzyme $Q_{10}$ crystal.

21. The process according to claim 1,
which further comprises, before the step of extracting the reduced coenzyme $Q_{10}$, disrupting the microbial cells under the condition that the reduced coenzyme $Q_{10}$ is protected from an oxidation reaction.

22. The process according to claim 21,
wherein the cell disruption is carried out by a physical treatment.

23. The process according to claim 22,
wherein the physical treatment is carried out by a high pressure homogenizer, an ultrasonic homogenizer, a French press or a ball mill.

24. The process according to claim 21,
wherein the cell disruption is carried out under an acidic to a weakly basic condition.

* * * * *